United States Patent [19]
Baker et al.

[11] Patent Number: 4,824,854
[45] Date of Patent: Apr. 25, 1989

[54] FUNGICIDAL PYRIDYL IMINOCARBONATES

[75] Inventors: Don R. Baker, Orinda; Keith H. Brownell, San Jose, both of Calif.

[73] Assignee: ICI Americas Inc., Wilmington, Del.

[21] Appl. No.: 114,808

[22] Filed: Oct. 29, 1987

[51] Int. Cl.$^4$ ............... C07D 213/64; C07D 213/74; A01N 43/40

[52] U.S. Cl. ................... 514/346; 514/352; 546/292; 546/305; 546/312; 546/261; 546/264; 546/283

[58] Field of Search ............... 546/292, 305, 312; 514/346, 352

[56] References Cited

U.S. PATENT DOCUMENTS 3,832,351 8/1974 Tanaka et al. ............... 546/305

Primary Examiner—Alan L. Rotman
Attorney, Agent, or Firm—Michael J. Bradley

[57] ABSTRACT

Novel fungicidal pyridyl iminocarbonates having the general structural formula

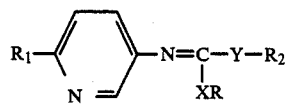

wherein
R is selected from the group consisting of $C_1$-$C_{16}$ alkyl, $C_3$-$C_8$ cycloalkyl, $C_2$-$C_8$ alkenyl, $C_2$-$C_8$ substituted alkenyl, $C_3$-$C_4$ carboalkoxyalkyl, aryl, arylalkyl having $C_1$-$C_3$ alkyl, substituted aryl and arylalkyl wherein the substituents are —Cl, —Br, —F and —NO$_2$; furfuryl, pyridyl, $C_1$-$C_6$ alkyl substituted phosphorus, alkanoyl, alkoxycarbonyl, aroyl, preferably benzoyl, alkylthioarbonyl, alkylthioalkyl, alkoxyalkyl, alkoxybenzyl and

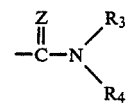

wherein
$R_3$ and $R_4$ are $C_1$-$C_{10}$ alkyl and can form a heterocyclic ring;
$R_1$ is selected from the group consisting of halogen, $C_1$-$C_3$ alkoxy, $C_3$-$C_4$ alkenyloxy and $C_1$-$C_3$ haloalkoxy;
$R_2$ is selected from the group consisting of $C_1$-$C_4$ alkyl;
X is sulfur or oxygen;
Y is sulfur or oxygen; and
Z is sulfur or oxygen;

and fungicidally acceptable organic and inorganic salts thereof which are highly effective fungicides for use both as preventive and curative fungicides are disclosed herein.

5 Claims, No Drawings

FUNGICIDAL PYRIDYL IMINOCARBONATES

BACKGROUND OF THE INVENTION

Fungal infection of crops such as barley, rice, tomatoes, wheat, beans, roses, grapes and other agriculturally important crops can cause heavy losses in both quantity and quality of agricultural products. It is therefore extremely desirable to have means of preventing, controlling or eliminating fungal growth. Much preventive spraying with commercial fungicides is conducted to attempt to prevent the establishment and growth of fungi on agriculturally important crops. It would also be desirable to have a curative fungicide which, on detection of fungal infection, could control the fungi and eliminate the deleterious effects by use of a post-infection curative spray.

SUMMARY OF THE INVENTION

Novel fungicidal pyridyl iminocarbonates having the formula

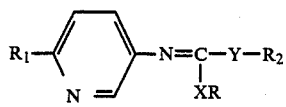

wherein
R is selected from the group consisting of $C_1$-$C_{16}$ alkyl, $C_3$-$C_8$ cycloalkyl, $C_2$-$C_8$ alkenyl, $C_2$-$C_8$ substituted alkenyl, $C_3$-$C_4$ carboalkoxyalkyl, aryl, arylalkyl having $C_1$-$C_3$ alkyl, substituted aryl and arylalkyl wherein the substituents are —Cl, —Br, —F and —$NO_2$, the preferred aryl and arylalkyl are phenyl, benzyl, phenethyl and naphthyl; furfuryl, pyridyl, $C_1$-$C_6$, preferably $C_1$-$C_4$, alkyl substituted phosphorus, alkanoyl, alkoxycarbonyl, aroyl, preferably benzoyl, alkylthioarbonyl, alkylthioalkyl, alkoxyalkyl, alkoxybenzyl, and

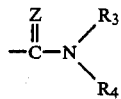

wherein $R_3$ and $R_4$ are $C_1$-$C_{10}$ alkyl and can form a heterocyclic ring;
$R_1$ is selected from the group consisting of halogen, such as chlorine, fluorine and bromine, $C_1$-$C_3$ alkoxy such as propoxy, ethoxy and methoxy, preferably methoxy, $C_3$-$C_4$ alkenyloxy and $C_1$-$C_3$ haloalkoxy;
$R_2$ is selected from the group consisting of $C_1$-$C_4$ alkyl, preferably methyl;
X is sulfur or oxygen;
Y is sulfur or oxygen; and
Z is sulfur or oxygen;
and fungicidally acceptable organic and inorganic salts thereof which are highly effective fungicides for use both as preventive and curative fungicides are disclosed herein.

The term "fungicide" is used to mean a compound which controls fungal growth. "Controls" includes prevention, destruction and inhibition of fungal growth. The term "curative" is meant to refer to a post infection application of a fungicide which establishes control of fungal infection and prevents development of deleterious effects of the fungi on the host crop.

DETAILED DESCRIPTION

The novel fungicidal compounds of this invention are pyridyl iminocarbonates having the general formula

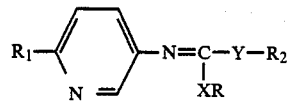

wherein
R is selected from the group consisting of $C_1$-$C_6$ alkyl, $C_3$-$C_8$ cycloalkyl, $C_2$-$C_8$ alkenyl, $C_2$-$C_8$ substituted alkenyl, $C_3$-$C_4$ carboalkoxyalkyl, aryl, arylalkyl having $C_1$-$C_3$ alkyl, substituted aryl and arylalkyl wherein the substituents are —Cl, —Br, —F and —$NO_2$, the preferred aryl and arylalkyl are phenyl, benzyl, phenethyl and naphthyl; furfuryl, pyridyl, $C_1$-$C_6$, preferably $C_1$-$C_4$, alkyl substituted phosphorus, alkanoyl, alkoxycarbonyl, aroyl, preferably benzoyl, alkylthioarbonyl, alkylthioalkyl, alkoxyalkyl, alkoxybenzyl and

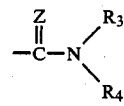

wherein $R_3$ and $R_4$ are $C_1$-$C_{10}$ alkyl and can form a heterocyclic ring;
$R_1$ is selected from the group consisting of halogen, such as chlorine, fluorine and bromine, $C_1$-$C_3$ alkoxy such as propoxy ethoxy and methoxy, preferably methoxy, $C_3$-$C_4$ alkenyloxy and $C_1$-$C_3$ haloalkoxy;
$R_2$ is selected from the group consisting of $C_1$-$C_4$ alkyl, preferably methyl;
X is sulfur or oxygen;
Y is sulfur or oxygen; and
Z is sulfur or oxygen;
and fungicidally acceptable organic and inorganic salts thereof which are highly effective fungicides for use both as preventive and curative fungicides are disclosed herein.

The compounds of this invention can be generally prepared by a multi-step reaction sequence. For the series of compounds were Y is oxygen, the first step comprises reaction of the properly substituted aminopyridine with thiophosgene in an inert solvent such as methylene chloride to form the pyridylisothiocyanate hydrochloride.

In the second reaction step, the pyridylisothiocyanate hydrochloride is reacted with a properly substituted alcohol and its alkoxide to form the pyridyl thionocarbamate.

In the third reaction step, the previously prepared pyridylthionocarbamate is alkylated or acylated under basic conditions with the properly substituted acid chloride, chloroformate, alkyl halide, benzyl halide or the like to give the desired N-pyridylimidothiocarbonate.

For the series of compounds where boty X and Y are sulfur the first step comprises reaction of the properly substituted aminopyridine with carbon disulfide in the presence of a teritary amine such as triethylamine. Alcohol facilitates the reaction. The resulting amine salt of the N-pyridyl dithiocarbamate is used in the second step of this reaction sequence. This salt is monoalkylated using an alkyl halide such as methyl iodide. Alkylation can also be effected by using a properly substituted sulfonate or sulfate. This yields the N-pyridyldithiocarbamate which can be further alkylated or acylated under basic conditions with the properly substituted acid chloride, chloroformate, alkyl halide, benzyl halide or the like. This yields the desired N-pyridylimidodithiocarbonate.

Pyridyl thioimidates of the invention are mildly basic. The unprotonated nitrogen atom of the pyridyl ring can be protonated by an acid, preferably either organic or inorganic. Representative inorganic acids or hydrochloric, nitric, hydrobromic, sulfuric, sulfamic and phosphoric. Representative organic acids are acetic, trifluoroacetic, benzoic, benzenesulfonic, p-toluenesulfonic, naphthalenesulfonic, phenylphosphonic and organophosphonic. The salts so formed are also fungicidal.

EXAMPLE 1

Preparation of 2-Methoxy-5-pyridyl isothiocyanate hydrochloride

5-Amino-2-methoxypyridine (11 ml, 0.10 mol) is added dropwise at reflux, with stirring to a solution of thiophosgene (8.4 ml, 0.11 mol) in methylene chloride. Refluxing is continued for a further hour and cooled to room temperature. The resulting solid is filtered off, washed with ether to give 9.6 g of the title intermediate product.

EXAMPLE 2

Preparation of O-Methyl-N-(2-methoxy-5-pyridyl)-thionocarbamate

2-Methoxy-5-pyridyl isothiocyanate hydrochloride (4.1 g, 0.02 mol), methanol (50 ml) and 25% sodium methoxide (9.1 ml, 0.04 mol) are mixed together in that order. The reaction was exothermic on addition of the sodium methoxide. The reaction is allowed to stand at room temperature for two hours and then concentrated in vacuo to a volume of approximately 10 ml, and then diluted with methylene chloride (100 ml). The reaction is washed with 10% aqueous acetic acid (100 ml), saturated sodium bicarbonate solution (50 ml); dried over anhydrous magnesium sulfate; filtered; and evaporated in vacuo to give an oil. This crystallized from pentane to yield 2.3 g of the title intermediate compound.

EXAMPLE 3

Preparation of O-Methyl-S-methyl-N-(2-methoxy-5-pyridyl)-imidothiocarbonate

Potassium t-butoxide (1.8 g, 0.012 mol) was added in one portion to O-methyl-N-(2-methoxy-5-pyridyl)-thionocarbonate (1.8 g, 0.010 mol) in dry tetrahydrofuran (40 ml) with stirring under a nitrogen atmosphere. After 10 minutes, methyl iodide (0.75 ml, 0.012 mol) was added and salt immediately formed in the light brown solution. After one hour, the reaction was diluted with methylene chloride (100 ml) and washed with water (2×100 ml); dried over anhydrous magnesium sulfate; filtered; and evaporated in vacuo to give 1.8 g of an oil. This was extracted with pentane (100 ml) and a small amount of insoluble solid filtered off and discarded. The filtrate was evaporated in vacuo to give 1.4 g of the title product as an oil. The title compound was identified by infrared (IR), nuclear magnetic resonance (NMR) spectra and mass-spectroscopic (MS) analysis.

EXAMPLE 4

Preparation of N-2-Methoxy-5-pyridyl)-dithiocarbamate triethylamine salt

Carbon disulfide (5.0 ml. 0–0.082 mol) was added in one portion to a solution of 5-amino-2-methoxypyridine (7.3 ml, 0.067 mol) 2-B ethanol (5.0 ml) and triethylamine (15.2 ml, 0.11 mol). The reaction is slightly exothermic and water bath cooling was applied. Two phases formed and after 30 minutes, solid formed. This was filtered off, washed with ethanol (30 ml) and acetone (20 ml) and dried in vacuo to give 19.2 g of the intermediate product, m.p. 83°–85° C.

EXAMPLE 5

Preparation of S-Methyl-N-(2-methoxy-5-pyridyl)-dithiolcarbamate

A solution of iodomethane (1.2 ml, 0.02 mol) was added in one portion to a mixture of methylenechloride (100 ml) and N-(2-methoxy-5-pyridyl)dithiocarbamate triethylamine salt (6.0 g, 0.02 mol). The reaction was exothermic to 28° C. The reaction was allowed to stand for 2 hours and washed with water (2×100 ml), saturated sodium bicarbonate (50 ml); dried over anhydrous magnesium sulfate; filtered; and evaporated in vacuo to give an oil. This was crystallized with pentane to give 3.5 g of solid as the title intermediate product, m.p. 85°–87° C. The title compound was identified by infrared (IR), nuclear magnetic resonance (NMR) spectra and mass-spectroscopic (MS) analysis.

EXAMPLE 6

Preparation of S,S'-Dimethyl-N-(2-methoxy-5-pyridyl)-imidodithiocarbonate

S-Methyl-N-(2-methoxy-5-pyridyl)-dithiocarbamate (2.0 g, 0.01 mol), tetrahydrofuran (50 ml), potassium t-butoxide (1.3 g, 0.012 mol) and methyliodide (0.75 ml, 0.012 mol) were mixed together in that order. The reaction was exothermic on addition of the methyl iodide. The reaction was stirred at room temperature for 1.5 hours and diluted with methylene chloride (150 ml) and washed with water (100 ml), saturated sodium bicarbonate (100 ml); dried over anhydrous magnesium sulfate; filtered and evaporated in vacuo to give an oil. This was extracted with pentane and evaporated in vacuo to give 2.0 g of a light yellow oil as the title compound. The title compound was identified by infrared (IR), nuclear magnetic resonance (NMR) spectra and mass-spectroscopic (MS) analysis.

EXAMPLE 7

Preparation of S-Methylthiocarbonyl-S'-methyl-N-(2-methoxy-5-pyridyl)-imidodithiocarbonate S-Methyl-N-(2-methoxy-5-pyridyl)-dithiolcarbamate (2.5 g, 0.012 mol) was added in portions to a stirred suspension of sodium hydride (0.3 g, 0.012 mol) in dry tetrahydrofuran (75 ml). The reaction was stirred for 1 hour and methyl chlorothiolformate (1.3 g, 0.012 mol) added. The reaction was stirred overnight and diluted with ether and water. The organic phase was washed with water; dried over anhydrous magnesium sulfate;

filtered; and evaporated in vacuo to yield 3.0 g of a brown oil as the title product. The title compound was identified by infrared (IR), nuclear magnetic resonance (NMR) spectra and mass-spectroscopic (MS) analysis.

Representative compounds of this invention and their properties are shown in Table I.

750 μg/ml. Twelve ml of test solution are sprayed onto the wheat plants with an atomizing sprayer.

A suspension of *Puccinia recondita* urediospores is prepared by vacuuming spores from wheat leaves with ureida pustules and suspending $10^5$ spores/ml in deionized water plus 0.5% Tween® 20 (polyoxyethylene

TABLE I $$R_1 \text{—} \underset{N}{\underset{\|}{\bigcirc}} \text{—} N=C-Y-R_2$$
$$\qquad\qquad\qquad |$$
$$\qquad\qquad\qquad XR$$

| Cmpd. No. | R | $R_1$ | $R_2$ | X | Y | Physical Form m.p. °C. |
|---|---|---|---|---|---|---|
| 1 | —CH$_3$ | —OCH$_3$ | —CH$_3$ | —S | —S | yellow oil |
| 2 | —CH$_2$OC$_2$H$_5$ | —OCH$_3$ | —CH$_3$ | —S | —S | yellow oil |
| 3 | —CH$_2$SCH$_3$ | —OCH$_3$ | —CH$_3$ | —S | —S | yellow oil |
| 4 | —C(=O)SCH$_3$ | —OCH$_3$ | —CH$_3$ | —S | —S | 83.0–88.0° C. |
| 5 | —C(=O)SCH(CH$_3$)$_2$ | —OCH$_3$ | —CH$_3$ | —S | —S | 64.0–67.0° C. |
| 6 | —CH$_2$OCH$_2$—C$_6$H$_5$ | —OCH$_3$ | —CH$_3$ | —S | —S | yellow oil |
| 7 | —C(=O)OCH$_3$ | —OCH$_3$ | —CH$_3$ | —S | —S | 79.0–83.0° C. |
| 8 | —C(=O)CH$_3$ | —OCH$_3$ | —CH$_3$ | —S | —S | yellow oil |
| 9 | —CH$_3$ | —OCH$_3$ | —CH$_3$ | —S | —O | yellow oil |

EXAMPLE 8

Preventive Spray Evaluation Procedures

Barley Powdery Mildew (PM)

Northrup King Sunbar 401 barley seed is planted (12 seeds/2" pot) in a sandy-loam soil seven days prior to testing. The test compound is diluted in a 50/50 acetone/water solution to produce concentrations decreasing from 750 μg/ml. The test solution is then sprayed onto the barley plants with atomizing sprayers.

Twenty-four hours later, test plants are placed in an inoculation box equipped with a circulating fan. Barley plants with heavily sporulating *Erysiphe graminis* lesions are placed in front of the fan to dislodge and distribute the spores. After two minutes the fan is shut off and the chamber is left closed five minutes for the spores to settle. Inoculated plants are then placed on an automatic sub-irrigation green-house bench.

Results are recorded seven days following inoculation as percent disease control based on the percent recuction in infected area as compared to the untreated control plants. Compound concentrations which provide 90% disease control (EC 90) are determined from dosage/dilution curves.

Leaf Rust (LR)

Seven seeds of Anza wheat are planted in 2" pots in a sandy-laom soil 12 days prior to testing. The compound to be tested is diluted with a 50/50 acetone/water solution to produce concentrations decreasing from sorbitan monolaurate). Plants are inoculated 24 hours after treatment by spraying with the spore suspension to runoff, allowing it to dry on the leaves, respraying to runoff, and then placing the plants into a mist chamber. Following 48 hours in the mist, plants are moved to a subirrigation greenhouse bench.

Results are recorded ten days following inoculation as percent disease control based on the percent reduction in lesion area as compared to the untreated control plants. Compound concentrations which provide 90% disease control (EC 90) are determined from dosage/dilution curves.

Botrytis Blight (BB)

Two white rose petals are placed in a petri dish lined with wet filter paper. The compound to be tested is diluted with a 50/50 acetone/water solution to produce concentrations decreasing from 750 μg/ml. One half ml of test solution is atomized onto the petals, and allowed to dry.

Inoculum is prepared by adding a 5 mm plug from a two-week old *Botrytis cinerea* culture grown on Elliot's V-8 agar, to 10 ml sterile distilled water plus 0.5 ml grape juice. A 20 μl drop of this inoculum suspension is placed on each petal. Petri dishes with inoculated petals are stored in sealed plastic boxes to maintain saturated humidity.

Results are read four days following inoculation as a percent reduction in necrotic area compared to the acetone/water controls. Compound concentrations which provide 90% disease control (EC 90) are determined from dosage/dilution curves.

The results are presented in Table II as an approximate EC 90 in parts per million. The entry (750) indicates partial control at 750 ppm.

Rice Blast (RB)

Ten seeds of Calrose M-9 rice are planted in 2 inch pots in a sandy loam soil 12 days prior to testing. The compound to be tested in diluted in a 50/50 acetone/water solution to produce concentrations decreasing from 750 μg/ml. Twelve ml of test solution are sprayed onto the rice plants with atomizing sprayers.

Inoculum is produced from 3 week old cultures of *Pyricularia oryzae*, grown on Rice Polish agar. The agar is first flooded with deionized water, the spores rubbed off the surface, and then diluted to $5 \times10^5$ spore/ml in deionized water plus 0.05% Tween® 20. Plants are inoculated 24 hours after compound application, plants are inoculated by spraying with the spore suspension to runoff, allowing it to dry on the leaves, respraying to runoff, and then placing the plants into a dark mist chamber. Following 48 hours of mist, the plants are moved to an automatic subirrigation greenhouse bench.

Results are recorded seven days following inoculation as percent disease control based on the percent reduction in lesion area as compared to the untreated control plants. Compound concentrations which provide 90% disease control (EC 90) are estimated from dosage/dilution curves.

The results are presented in Table II as an approximate EC 90 in parts per million. 750 ppm equals 750 || g/ml. The entry (750) indicates partial control at 750 ppm. The entry "*" indicates no control at 750 ppm.

TABLE II

| Cmpd. No. | PM | LR | BB | RB |
|---|---|---|---|---|
| 1 | * | (750) | 750 | * |
| 2 | * | * | 750 | (750) |
| 3 | (750) | * | * | * |
| 4 | (750) | (750) | (750) | * |
| 5 | * | * | (750) | * |
| 6 | * | * | (750) | * |
| 7 | * | * | (750) | * |
| 8 | * | 750 | 750 | * |
| 9 | * | 750 | (750) | * |

The compounds of the present invention are useful as fungicides, especially as preventative or curative fungicides, and can be applied in a variety of ways at various concentrations. In general, those compounds and formulations of these compounds can be applied directly to the crop foliage, the soil in which the crop is growing or in the irrigation water for the crop or soil. In practice, the compounds herein defined are formulated into fungicidal compositions, by admixture, in fungicidally effective amounts, which the adjuvants and carriers normally employed for facilitating the dispersion of active ingredients for agricultural applications, recognizing the fact that the formulation and mode of application of a toxicant may affect the activity of the materials in a given application. Thus, these active fungicidal compounds may be formulated as wettable powders, as emulsifiable concentrates, as powdery dusts, as solutions or as any of several other known types of formulations, depending upon the desired mode of application. Preferred formulations for preventative or curative fungicidal applications are wettable powders and emulsifiable concentrates. These formulations may contain as little as about 0.5% to as much as about 95% or more by weight of active ingredient. A fungicidally effective amount depends upon the nature of the seeds or plants to be treated and the rate of application varies from about 0.05 to approximately 25 pounds per acre, preferably from about 0.1 to about 10 pounds per acre.

Wettable powders are in the form of finely divided particles which disperse readily in water or other dispersants. The wettable powder is ultimately applied to the soil or plants either as a dry dust or as a dispersion in water or other liquid. Typical carriers for wettable powders include Fuller's earth, kaolin clays, silicas and other readily wet organic or inorganic diluents. Wettable powders normally are prepared to contain about 5% to about 95% of the active ingredient and usually also contain a small amount of wetting, dispersing, or emulsifying agent facilitate wetting and dispersion.

Dry flowables or water dispersible granules are agglomerated wettable powders made by either pan granulation or by fluidized bed. The dry flowable is ultimately applied to the soil or plants as a dispersion in water or other liquid. These granules are dust-free and free flowing when dry and yet upon dilution in water, form homogeneous dispersions. Typical carriers for dry flowables include fuller's earth, kaolin clays, clays, silicas and other readily wet organic or inorganic diluents. The dry flowables normally are prepared to contain from about 5% to about 95% of the active ingredient and usually contain a small amount of wetting, dispersing or emulsifying agent to facilitate wetting and dispersion.

Emulsifiable concentrates are homogeneous liquid compositions which are dispersible in water or other dispersant, and may consist entirely of the active compound with a liquid or solid emulsifying agent, or may also contain a liquid carrier, such as xylene, heavy aromatic naphtha, isophorone and other non-volatile organic solvents. For fungicidal application, these concentrates are dispersed in water or other liquid carrier and normally applied as a spray to the area to be treated. The percentage by weight of the essential active ingredient may vary according to the manner in which the composition is to be applied, but in general comprises about 0.1% to 95% of active ingredient by weight of the fungicidal composition.

Typical wetting, dispersing or emulsifying agents used in agricultural formulations include, for example, the alkyl and alkylaryl sulfonates and sulfates and their sodium salts; polyhydroxy alcohols; and other types of surface-active agents, may of which are available in commerce. The surface-active agent, when used, normally comprises from 0.1% to 15% by weight of the fungicidal composition.

Dusts, which are free-flowing admixtures of the active ingredient with finely divided solids such as talc, clays, flours and other organic and inorganic solids which act as dispersants and carriers for the toxicant, are useful formulations for many applications.

Pastes, which are homogeneous suspensions of a finely divided solid toxicant in a liquid carrier such as water or oil, are employed for specific purposes. These formulations normally contain about 5% to about 95% of active ingredient by weight, and may also contain small amounts of a wetting, dispersing or emulsifying agent to facilitate dispersion. For application, the pastes are normally diluted and applied as a spray to the area to be affected.

EXAMPLES OF TYPICAL FORMULATIONS

| Ingredient | Weight % |
|---|---|
| Oil | |
| Compound 1 | 1 |
| Oil solvent-heavy aromatic naphtha | 99 |
| Total | 100 |
| Emulsifiable Concentrate | |
| Compound 2 | 50 |
| Kerosene | 45 |
| Emulsifying agent (mixture of long chain ethoxylated polyethers with long chain sulfonate) | 5 |
| Total | 100 |
| Compound 3 | 90 |
| Kerosene | 5 |
| Emulsifying agent (mixture of long chain ethoxylated polyethers with long chain sulfonate) | 5 |
| Total | 100 |

| Dusts and/or Powders | | | |
|---|---|---|---|
| Ingredient | Wt. % | Wt. % | Wt. % |
| Compound 1 | 0.5 | 50.0 | 90.0 |
| Attapulgite Clay Powder | 93.5 | 44.0 | 4.0 |
| Sodium lignin sulfonate | 5.0 | 5.0 | 5.0 |
| Sodium dioctyl sulfosuccinate | 1.0 | 1.0 | 1.0 |
| Total | 100.0 | 100.0 | 100.0 |

Other useful formulations for fungicidal applications include simple solutions of the active ingredient in a dispersant in which it is completely soluble at the desired concentration, such as acetone, alkylated naphthalenes, xylene and other organic solvents. Pressurized sprays, typically aerosols, wherein the active ingredient is dispersed in finely divided form as a result of vaporization of a low boiling dispersant solvent carrier, such as the Freons, may also be used.

The fungicidal compositions of this invention are applied to the plants in the conventional manner. Thus, the dust and liquid compositions can be applied to the plant by the use of power-dusters, boom and hand sprayers and spray dusters. The compositions can also be applied from airplanes as a dust or a spray because they are effective in low dosages.

We claim:

1. A compound having the structural formula

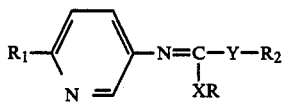

wherein

R is selected from the group consisting of $C_1$–$C_{16}$ alkyl, $C_3$–$C_8$ cycloalkyl, $C_2$–$C_8$ alkenyl, $C_2$–$C_8$ substituted alkenyl wherein the substituents are selected from the group consisting of —Cl, —Br, —F and —NO$_2$;

$R_1$ is selected from the group consisting of halogen, $C_1$–$C_3$ alkoxy, $C_3$–$C_4$ alkenyloxy and $C_1$–$C_3$ haloalkoxy;

$R_2$ is $C_1$–$C_4$ alkyl;

X is sulfur or oxygen;

Y is sulfur or oxygen; or a fungicidally acceptable organic or inorganic salt thereof.

2. The compound of claim 1 wherein R is —CH$_3$, $R_1$ is —OCH$_3$, $R_2$ is —CH$_2$, X is —S and Y is —S.

3. A fungicidal composition comprising a fungicidally effective amount of a compound having the structural formula

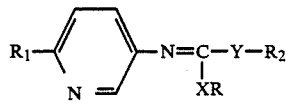

wherein

R is selected from the group consisting of $C_1$–$C_6$ alkyl, $C_3$–$C_8$ cycloalkyl, $C_2$–$C_8$ alkenyl, $C_2$–$C_8$ substituted alkenyl wherein the substituents are selected from the group consisting of —Cl, —Br, —F and —NO$_2$;

$R_1$ is selected from the group consisting of halogen, $C_1$–$C_3$ alkoxy, $C_3$–$C_4$ alkenyloxy and $C_1$–$C_3$ haloalkoxy;

$R_2$ is $C_1$–$C_4$ alkyl;

X is sulfur or oxygen;

Y is sulfur or oxygen; or a fungicidally acceptable organic or inorganic salt thereof in admixture with a carrier or diluent therefor.

4. The method of controlling fungi comprising applying to the area where control is desired, a fungicidally effective amount of a compound having the formula

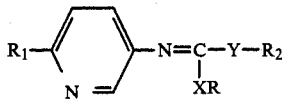

wherein

R is selected from the group consisting of $C_1$–$C_{16}$ alkyl, $C_3$–$C_8$ cycloalkyl, $C_2$–$C_8$ alkenyl, $C_2$–$C_8$ substituted alkenyl wherein the substituents are selected from the group consisting of —Cl, —Br, —F and —NO$_2$;

$R_1$ is selected from the group consisting of halogen, $C_1$–$C_3$ alkoxy, $C_3$–$C_4$ alkenyloxy and $C_1$–$C_3$ haloalkoxy;

$R_2$ is $C_1$–$C_4$ alkyl;

Y is sulfur or oxygen;

Y is sulfur or oxygen;

or a fungicidally acceptable organic or inorganic salt thereof.

5. The method of claim 4 wherein R is —CH$_3$, $R_1$ is —OCH$_3$, $R_2$ is —CH$_3$, X is —S and Y is —S.

* * * * *

UNITED STATES PATENT AND TRADEMARK OFFICE
CERTIFICATE OF CORRECTION

PATENT NO. : 4,824,854
DATED : April 25, 1989
INVENTOR(S) : Don R. Baker and Keith H. Brownell It is certified that error appears in the above-indentified patent and that said Letters Patent is hereby corrected as shown below:

In Column 10, line 21, "$C_1-C_6$" should read --$C_1-C_{16}$--.

Signed and Sealed this

Twenty-ninth Day of March, 1994

Attest:

BRUCE LEHMAN

*Attesting Officer*  Commissioner of Patents and Trademarks